(12) United States Patent
Manic et al.

(10) Patent No.: US 12,240,800 B2
(45) Date of Patent: Mar. 4, 2025

(54) MULTIPRODUCT LOW BIURET UREA PRODUCTION

(71) Applicant: Stamicarbon B.V., Sittard (NL)

(72) Inventors: Branislav Manic, Maastricht (NL); Rahul Patil, Maastricht (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 18/692,124

(22) PCT Filed: Nov. 22, 2023

(86) PCT No.: PCT/NL2023/050611
§ 371 (c)(1),
(2) Date: Mar. 14, 2024

(87) PCT Pub. No.: WO2024/112197
PCT Pub. Date: May 30, 2024

(65) Prior Publication Data
US 2024/0262789 A1    Aug. 8, 2024

(30) Foreign Application Priority Data
Nov. 22, 2022 (EP) .................................... 22208916

(51) Int. Cl.
*B01D 1/00* (2006.01)
*C07C 273/12* (2006.01)
*C07C 273/16* (2006.01)
*C07D 251/60* (2006.01)

(52) U.S. Cl.
CPC .......... *C07C 273/12* (2013.01); *B01D 1/0088* (2013.01); *C07C 273/16* (2013.01); *C07D 251/60* (2013.01)

(58) Field of Classification Search
CPC ... C07C 273/12; C07C 273/16; C07D 251/60; B01D 1/0088
See application file for complete search history.

(56) References Cited

U.S. PATENT DOCUMENTS

| | | | |
|---|---|---|---|
| 9,458,098 B2 * | 10/2016 | Mennen | B01J 10/00 |
| 10,457,633 B2 * | 10/2019 | Mostert | C07C 273/16 |
| 10,526,281 B2 * | 1/2020 | Mostert | C07C 273/04 |
| 10,882,820 B2 * | 1/2021 | Mostert | C07C 273/04 |
| 11,332,437 B2 * | 5/2022 | Patil | B01D 5/0003 |
| 11,420,937 B2 * | 8/2022 | Patil | B01D 5/0027 |

(Continued)

FOREIGN PATENT DOCUMENTS

| | | |
|---|---|---|
| CN | 209669101 | 11/2019 |
| CN | 111606867 | 9/2020 |

(Continued)

OTHER PUBLICATIONS

International Search Report and Written Opinion in PCT Application No. PCT/NL2023/050611, mailed Feb. 22, 2024 (9 pages).

(Continued)

*Primary Examiner* — Jonathan Miller
(74) *Attorney, Agent, or Firm* — Leason Ellis LLP

(57) ABSTRACT

Embodiments pertain to a urea plant and to the operation of a urea plant in a reduced load mode. In embodiments, two evaporators in parallel are used, connected to a finishing section respectively to a melamine plant.

15 Claims, 1 Drawing Sheet

(56) References Cited

U.S. PATENT DOCUMENTS

| | | |
|---|---|---|
| 11,905,234 B2* | 2/2024 | Patil ................. B01D 53/58 |
| 2004/0116743 A1 | 6/2004 | Mennen |
| 2004/0162429 A1* | 8/2004 | Noe .................. C07D 251/60 |
| | | 544/201 |
| 2009/0084149 A1 | 4/2009 | Van Der Werf et al. |
| 2009/0216045 A1 | 8/2009 | Singh |
| 2015/0133690 A1* | 5/2015 | Mennen ................. B01J 10/00 |
| | | 422/187 |
| 2016/0318883 A1 | 11/2016 | Mennen |
| 2017/0204054 A1 | 7/2017 | Mennen |
| 2019/0210963 A1 | 7/2019 | Mostert |
| 2022/0089528 A1* | 3/2022 | Patil ................. C07C 273/16 |

FOREIGN PATENT DOCUMENTS

| | | |
|---|---|---|
| CN | 212476589 | 2/2021 |
| EP | 2385043 | 11/2011 |
| WO | 2004011419 | 2/2004 |
| WO | 2016153354 | 9/2016 |

OTHER PUBLICATIONS

Ullmann's Encyclopaedia, chapter Urea, 2010.
Ullmann's Encyclopedia of Industrial Chemistry, vol. 21, chapter Melamine and Guanamines, 2003.

\* cited by examiner

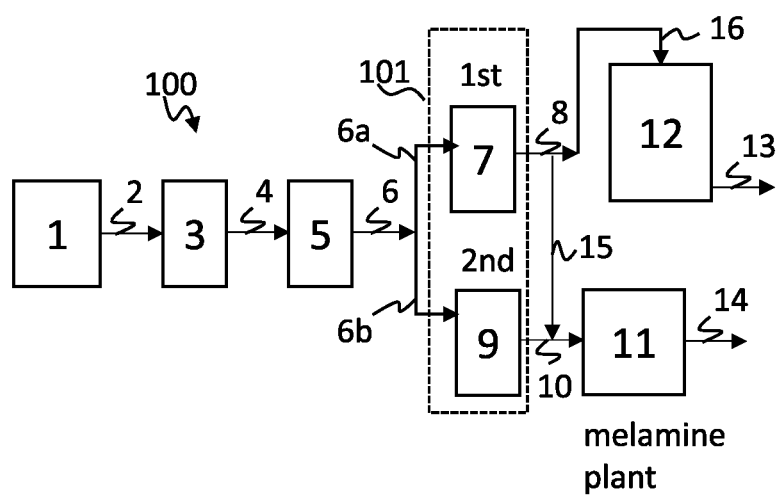

MULTIPRODUCT LOW BIURET UREA PRODUCTION

CROSS-REFERENCE TO RELATED PATENT APPLICATIONS

This application is a U.S. National Stage Application under 35 U.S.C. § 371 of International Patent Application No. PCT/NL2023/050611, filed Nov. 22, 2023, which claims the benefit of priority of European Patent Application No. 22208916.1, filed Nov. 22, 2022, both of which are incorporated by reference in their entireties.

FIELD

The invention pertains to a urea manufacturing process, and a plant suitable for such process, that allows controlling biuret formation also in the event that the plant is operated at a reduced capacity.

INTRODUCTION

Various types of urea production processes are described in Ullmann's Encyclopedia, chapter Urea, 2010. As described therein, biuret is an undesirable byproduct formed in urea plants.

US 2004/0116743A1 describes the turndown ratio of a urea plant as the minimum load on which a plant can be operated without turn-down time. The document mentions that operation at minimum load may be necessary if the supply of raw materials is disrupted or strongly reduced.

US 2019/0210963A1 describes a method of controlling the formation of biuret in urea production by controlling the residence time of a urea aqueous stream treated in such concentration section in a manner independently of the volume flow per time interval of said stream into said concentration section. The residence time can be controlled, e.g., by providing the concentration section with an adjustable volume or by adding a gas to the urea stream to be treated.

One of the challenges in urea production concerns controlling the amount of biuret formed as a by-product, and generally present in urea products such as prills or granules. Biuret is dimer of urea, and is formed under release of ammonia. The amount of biuret is an indicator of the urea quality as can be sold. Biuret in urea used as a fertilizer is above certain levels detrimental for at least various types of plants. Biuret levels must be even lower for technical grade urea and urea used for NOx selective catalytic reduction.

Typically, a worldwide standard specification for biuret in urea products, is below 1 wt. 0%. For example, for fertilizer purposes, the amount of biuret is generally below 0.9 wt. %. For other applications, such as the use of an aqueous urea solution in a unit for the reduction of NOx in diesel exhaust gases (particularly known as Diesel Exhaust Fluid) the biuret content is required to be still lower.

A standard for DEF is ISO 22241-1:2006 (version of 15 Oct. 2006). DEF should have low biuret content. DEF refers to an aqueous solution of urea for use in the selective catalytic reduction of NOx from exhaust gas (SCR solution). ISO 22241-1:2006 specifies biuret as max. 0.3 wt. % on the basis of 31.8 wt. % urea aqueous solution, giving a limit of 0.95 wt. % biuret for solid urea (which can be diluted by adding demineralized water to 31.8 wt. % urea solution). A biuret level of less than 0.85 wt. % biuret is desirable for solid urea products, especially for fertilizer grade. Taking into account the formation of biuret in other parts of the urea production process, this gives a budget for biuret formation in a second vacuum evaporation stage of max. 0.20 wt. %, and desirably lower, for urea melt used for making solid urea product with acceptable low biuret content.

A problem in the art of urea production is that it is more difficult to produce urea according to desired biuret specifications, in the event that the plant in which the urea is produced, is not operated on full capacity. Generally, biuret levels are guaranteed for a plant operating at full capacity. In practice, this means that manufacturers operating their plants at reduced capacity, run a risk that the products produced do not meet specifications for all end-uses. It would be desired to provide a urea manufacturing process, and a plant suitable for such process, that allows controlling biuret formation also in the event that the plant in which the urea is produced is operated at a reduced capacity.

Operating a urea plant at less than full capacity may be necessary or desirable in case of lower demand and/or reduced availability of feedstock, such as reduced availability of natural gas or coal used for making hydrogen that is used for the synthesis of the $NH_3$ feed of the urea plant.

SUMMARY

The invention provides a plant for the production of urea which is capable of operating at a reduced load mode while still producing urea melt having low biuret content Operation at reduced load refers to operation at less than full capacity, in terms of urea production rate (ton/hr urea). It is desired to provide a plant capable of operating in at least a first and a second mode, wherein the urea production rate is lower in the second mode than in the first mode. The plant is desirably able to switch from the first to the second mode, and back. Corresponding methods also desired, in particular methods of operating a urea plant in a reduced load mode and methods of switching from the first to the second operating mode. Embodiments of the present invention provide such plants and methods.

The invention pertains in a first aspect to a method of operating a urea plant in a reduced load mode, the method comprising: operating a high pressure urea synthesis section of a urea plant in a reduced load mode; subjecting a urea solution stream from the urea synthesis section to purification in a recovery section to give purified urea solution; subjecting the purified urea solution to evaporation of water in a first vacuum evaporation stage, to give a first concentrated urea solution; subjecting a first part of the first concentrated urea solution to evaporation of water in a first evaporator of a second vacuum evaporation stage to form a first urea melt; subjecting a second part of the first concentrated urea solution to evaporation of water in a second evaporator of the second vacuum evaporation stage to form second urea melt. In the method, preferably the first evaporator is operated at a first operating capacity ratio, as percentage of the design capacity of the first evaporator, and wherein the second evaporator is operated at a second operating capacity ratio, as percentage of the design capacity of the second evaporator, wherein the second operating capacity ratio is lower than the first operating capacity ratio, and wherein the second evaporator has an outlet for the second urea melt in connection with an inlet of a melamine plant. Hence, the second evaporator is connected with the melamine plant to supply the second urea melt to the melamine plant.

The invention pertains further to a plant for the production of urea, comprising: a urea production section comprising a synthesis section and a recovery section, a first vacuum evaporation stage receiving urea solution from the urea production section, a second vacuum evaporation stage receiving concentrated urea solution from the first vacuum evaporation stage, comprising a first evaporator and a second evaporator arranged in parallel, both receiving concentrated urea solution from the first vacuum evaporation stage, wherein the first evaporator has an outlet for first urea melt connected to a finishing section and to a melamine plant, and wherein the second evaporator has an outlet for urea melt connected to said melamine plant.

The invention pertains further to a method of switching a urea plant, preferably an inventive urea plant, from a first mode to a second mode wherein the urea production rate is higher in the first mode than in the second mode, the method comprising decreasing the flow rate of concentrated urea solution (6b) to the second evaporator (9); and keeping the flow rate of concentrated urea solution (6a) to the first evaporator (7) constant, or increasing the flow rate of concentrated urea solution to the first evaporator, or decreasing the flow rate of concentrated urea solution to the first evaporator in such an amount that the decrease, relative to the flow rate of the first evaporator in the first mode, is smaller than the decrease of the flow rate of concentrated urea solution to the second evaporator relative to the flow rate of the second evaporator in the first mode.

In summary embodiments pertain to the operation of a urea plant in a reduced load mode. In embodiments, an evaporation stage with two evaporation sections or evaporators in parallel is used, wherein this evaporation stage is connected to a finishing section and to a melamine plant. In embodiments, two evaporators in parallel are used, connected to a finishing section respectively to a melamine plant.

BRIEF DESCRIPTION OF THE DRAWINGS

FIG. 1 schematically illustrates an example urea plant according to the invention.

Any embodiments illustrated in the figures are examples only and do not limit the invention.

DETAILED DESCRIPTION

Advantageously in the present invention, the biuret content of the first urea melt from the first evaporator of the second vacuum evaporation stage is relatively low, even if the plant is operated in a reduced load mode. In particular, the residence time in the first evaporator is relatively short, in particular shorter than in the parallel second evaporator of the second vacuum evaporation stage, which provides for relatively low biuret content. The first urea melt can therefore be used for making highly pure urea products, such as, e.g. high purity solid urea product, for instance as urea prills, or for making Diesel Exhaust Fluid (DEF) of for a urea product that can be diluted to DEF by adding demineralized water. Very elegantly, the relatively high biuret content of the second urea melt from the second evaporator does not affect or upset the melamine product and does not lead to any contamination of the melamine product. Generally, because of the higher temperature and lower $NH_3$ level of the urea solution in the second vacuum evaporation stage compared to the upstream first vacuum evaporation stage, biuret formation is more significant in the second vacuum evaporation stage.

The high ammonia level at one or more stages of the melamine production causes the biuret to react to urea which is then processed in the melamine plant.

The invention pertains to a method of operating a urea plant in a reduced load mode, in particular a reduced load operating mode. This method can also be described as a urea production method.

A reduced load operating mode indicates operation of the plant at less than the design capacity of the plant in terms of urea production rate, for instance at less than 95% of design capacity, such as at less than 90% or less than 80% of design capacity, typically at more than 40% or more than 50%, or more than 60%.

A reduced load operating mode indicates operating the plant, in particular the urea synthesis section, with a urea production rate in the range between the turndown rate (the minimum production rate) and up to, but lower than, the design capacity of the plant respectively urea synthesis section.

Various aspects of the inventive method will now be discussed using, for convenience, references to FIG. 1, which FIGURE illustrates an example method and plant according to the invention; the FIGURE and references thereto do not limit the claims or the invention.

The method comprises operating the high pressure synthesis section (1) of the urea plant (100), reacting $CO_2$ and $NH_3$ to form urea. Typical reaction conditions are a pressure of 12 to 40 MPa and a pressure between 150° C. and 250° C.

The urea synthesis section is operated in particular in a reduced load mode, i.e. with a lower urea production rate than design capacity, for instance with a production rate of less than 95% or less than 90% or less than 80% of the design capacity, and of for instance at least 40% or at least 50% of the design capacity.

The urea synthesis section is for instance of the stripping type, wherein the synthesis section comprises a reaction zone, a stripper, and a condensation zone. The reaction zone and condensation zone can be combined in a single vessel but can also be provided as separate vessels. The reaction zone and the condensation zone can each be provided by multiple units. The stripper uses for instance thermal stripping or $CO_2$ stripping. A stripper is typically a shell-and-tube heat exchanger configured for a falling film of urea solution in the tubes and heating fluid in the shell, with an inlet for urea solution at the top, an outlet for stripped urea solution at the bottom, and an outlet for a gas stream to the HP condenser at the top. The stripper is e.g. a $CO_2$ stripper or thermal stripper. A HP carbamate condenser providing the condensation zone is for instance a shell-and-tube heat exchanger, with gas to be condensed in the shell or in the tubes. A reactor of a synthesis section is for example a vertical reactor with trays, with one or more inlets at the bottom and an outlet for withdrawing urea solution from the top. In an example embodiment, the condensation zone and reaction zone are combined in a single horizontal vessel, e.g. a pool reactor.

Also urea synthesis sections without a HP stripper can be used, known as conventional processes in the art.

The HP urea synthesis section may comprise two or more reaction zones, e.g. urea reactors, in parallel, and/or in series. The use of two or more urea reactors in parallel may contribute to flexible operation in reduced load operating mode.

The method involves subjecting a urea solution stream (2) from the synthesis section (1) to purification in a recovery section (3) to give purified urea solution (4). The recovery section is for instance operated at MP and/or LP. The recovery section comprises e.g. an MP and an LP section in series, or an LP recovery section having an inlet for urea solution connected to an outlet for urea solution of the HP urea synthesis section. In the recovery section, unreacted carbamate is decomposed into $CO_2$ and $NH_3$ which are, preferably, condensed as carbamate solution that is recycled, directly or indirectly, in part or entirely to the synthesis section. The recovery section comprises typically an LP dissociator, and for instance comprises two LP dissociation units (decomposers) in parallel.

The method involves subjecting the purified urea solution (4) to evaporation of water in a first vacuum evaporation stage (5), to give a first concentrated urea solution (6). The concentrated urea solution for instance has a water content of 1.0-20 wt. %, preferably 1-5 wt. %, and/or preferably has a urea content (including biuret) of e.g. 85 to 98 wt. %.

The first vacuum evaporation stage (5) is for instance operated with a pressure of 0.10-0.50 bar absolute.

The first vacuum evaporation stage (5) may comprise, for example, two or more evaporators, in particular in parallel. The term 'first vacuum evaporation stage' does not imply the absence of vacuum evaporation units upstream of the section. For instance, a pre-evaporation section operating at a pressure below 1 bar absolute and configured for heating the urea solution to effect evaporation of water may be present in the recovery section or between the recovery section and the first vacuum evaporation stage.

In embodiments, the first concentrated urea solution (6) is divided in at least a first and a second part. In other embodiments with parallel evaporators in the first vacuum evaporation stage (5), a first one of said parallel evaporators may provide the first part (6a) of the first concentrated urea solution and a second of said evaporators may provide the second part (6b) of the first concentrated urea solution. Optionally, a further third part of the concentrated urea solution (6) is supplied to an additional finishing section (not shown in the FIGURE), bypassing the second vacuum evaporation stage (101). The additional finishing section is for instance a type of granulator capable of using concentrated urea solution with e.g. 92 wt. %-98 wt. % urea as granulation liquid. Hence, in some embodiments, the plant comprises two finishing sections in parallel.

The method involves subjecting a first part (6a) of the first concentrated urea solution to evaporation of water in a first evaporator (7) of a second vacuum evaporation stage (101) to form a first urea melt (8). The water content is reduced by e.g. at least 0.1% point by weight, such as by at least 1.0% point by weight. The water content of the first urea melt is e.g. less than 0.50 wt. %. The first urea melt comprises e.g. at least 99.5 wt. % urea including biuret. The first evaporator (7) is for instance operated at a pressure of less than 0.20 bar absolute, e.g. between 0.01 and 0.015 bar absolute, or in case the finishing section is a prilling tower, for example less than 0.05 bara. The first urea melt is preferably suitable for solidification in a finishing section, more preferably for prilling.

The first evaporator is e.g. a shell-and-tube heat exchanger, for example with urea solution in the tubes, and preferably with the inlet for urea solution at the bottom of the tubes and with gas/liquid separation at the upper end of the tubes. A heating fluid is present in the shell, for instance steam, or for instance gaseous streams comprising $CO_2$ and $NH_3$ that are condensed under the exothermic formation of carbamate.

The method involves subjecting a second part (6b) of the first concentrated urea solution to evaporation of water in a second evaporator (9) of the second vacuum evaporation stage (102). Preferences for the construction, pressure and water content specified for the first evaporator apply also for the second evaporator (9). The second urea melt comprises e.g. at least 99.5 wt. % urea including biuret.

The second evaporator has an outlet for second urea melt (10), i.e. a second urea melt stream, connected to an inlet of a melamine plant (11) also having an outlet of melamine melt (14). The method preferably involves supplying a part or all of the second urea melt to the melamine plant; e.g. at least 50 wt. % or at least 90 wt. % of the second urea melt is supplied to the melamine plant. In some embodiments, the method also involves producing melamine in the melamine plant, using the second urea melt as a part or all of the feedstock. In some embodiments, the melamine plant also receives urea melt from an additional urea plant. The melamine production is based on the pyrolysis of urea into melamine. The type of melamine plant is not particularly limited. Both high pressure (>70 bar abs.) non-catalytic melamine processes and low pressure catalytic processes (<70 bar abs.) can be used. Various suitable melamine processes are described in Ullmann's Encyclopedia of Industrial Chemistry, volume 21, chapter Melamine and Guanamines, 2003. Further examples of especially suitable melamine production plants are described in US20040162429A1, EP2385043A1 and EP3597641. However, other types of melamine plants can also be used. Off-gas from the melamine plant is preferably supplied to the urea production plant, optionally after condensation. Some example configurations for the supply of the off-gas to the urea plant are described in US20160318883A1.

In the inventive method, the first evaporator (7) is operated at a first operating capacity ratio, as percentage of the design capacity of the first evaporator, and the second evaporator (9) is operated at a second operating capacity ratio, as percentage of the design capacity of the second evaporator. The second operating capacity ratio is smaller than the first operating capacity ratio. For instance, the second operating capacity ratio at least 5 percentage point or at least 10 percentage point lower than the first operating capacity ratio. For instance, the first evaporator is operating at 100% of its design capacity, and the second evaporator is operating at 50% of design capacity. By way of further example, the urea production is 80 ton/hr in reduced load mode, with 60 ton/hr to the first evaporator and 20 ton/hr to the second evaporator. In full load mode, the urea production is 100 ton/hr, with 60 ton/hr to the first evaporator and 40 ton/hr to the second evaporator. All urea from the second evaporator is supplied to the melamine plant. At least a part of the urea from the first evaporator is sent to, e.g., prilling. In reduced load mode, the residence time of the urea solution in the second evaporator will be longer (twice, in the given example) leading to formation of relatively much biuret, which is however not detrimental to the operation of the melamine plant. The residence time increases by the constant liquid volume in the evaporator and the lower throughput. Residence time of urea solution in the first evaporator is the same in full load and reduced load mode, such that biuret content of the prills does not increase. A part of the urea melt from the first evaporator can be supplied to the melamine plant as necessary, e.g. 20 ton/hr to provide for stable operation of the melamine plant. The design capacity of the first evaporator may be larger, smaller, or the same as the design capacity of the second evaporator. The design capacity can also be referred to as the load of the unit in a full load operating mode of the plant.

The method for instance involves simultaneously supplying a first part of the first urea melt (8), i.e. first urea melt stream, to the melamine plant and a second part to a finishing section. The first and second urea melts, respectively first and second urea melt streams, are separate streams, suitably transported through different flow lines (such as pipes and tubes).

In the reduced load mode, the residence time for urea solution in the second evaporator is longer than in the first evaporator.

The biuret content of the second urea melt is for instance at least 0.02 wt. % (percentage point) or at least 0.05 wt. % (percentage point) higher than in the first urea melt. The biuret formation in the second evaporator is e.g. 0.20-0.30 wt. %, and the biuret formation in the first evaporator is e.g. 0.10-0.20 wt. %. The biuret content in the second urea melt is e.g. higher than permitted for the prilling or other use of the first urea melt.

In example embodiments, the biuret formation in full load operation mode is each, in the range 0.1-0.20 wt. % for each of the first and second evaporator (amount of biuret formed relative to the urea melt at the outlet).

The flow rate of urea solution to the first evaporator may be higher than, equal to, or smaller than the flow rate to the second evaporator, depending on the respective design capacities of the evaporators.

In some embodiments, the first evaporator is operated at 90-100% of the design capacity of the first evaporator, and the second evaporator is operated at 20-80% of the design capacity of the second evaporator. These ranges may be used in addition to, or instead of, the first and second operating capacity ratio.

Preferably, the first evaporator (7) is connected to supply all or a part of the first urea melt (8) to a urea finishing section (12), configured to form a solid urea product (13). The finishing section comprises, for example, a granulator, prilling tower, or pastillation unit, or a combination thereof.

Optionally, the first evaporator (7) is also connected to supply a part (15) of the first urea melt (8) to the melamine plant (11). The method involves supplying all or a part (16) of the first urea melt (8) to the urea finishing section (12), and preferably supplying a part (15) of the first urea melt (8) to the melamine plant (11). Thereby the urea supply to the melamine plant can be kept stable, even when reducing the urea production in the urea synthesis section, which stabilizes the operation of the melamine plant.

In some embodiments, the method involves subjecting a part or all of the first urea melt (8) to prilling in a prilling tower.

Prilling is preferred for the finishing section, because typically no additive, such as formaldehyde, is necessary for prilling. In some embodiments, the method involves scrubbing exhaust air from the prilling tower in a dust scrubber, to remove urea dust from it, yielding an aqueous urea solution as spent scrub liquid, and supplying the spent scrub liquid to a point upstream of the inlet for urea solution of the first vacuum evaporation stage and/or upstream of the inlet for concentrated urea solution of the second vacuum evaporation stage.

In some embodiments, the scrubbing from which the spent scrub liquid is obtained does not involve acid scrubbing and the spent scrub liquid contains no ammonium salts of mineral acids, in particular contains no ammonium nitrate and no ammonium sulphate. Optionally, the gas stream from the dust scrubber is further subjected to acid scrubbing in a separate downstream acid scrub unit, yielding a liquid stream comprising dissolved ammonium salts. This liquid stream can be disposed of as known in the art, e.g., to form ammonium sulphate solid product or urea ammonium nitrate solution. In some embodiments, exhaust air from the finishing section, such as prilling tower or granulator, is subjected to scrubbing involving both dust and acidic scrubbing, yielding a liquid stream comprising urea and ammonium salts. This liquid stream can be disposed of as known in the art, e.g. to form solid urea ammonium sulphate or liquid urea ammonium nitrate; using e.g. a dedicated evaporation section, separate from the first and second vacuum evaporation stage, to form concentrated spent scrub liquid which can be combined with the urea melt supplied exclusively to the finishing section, i.e. downstream of the split between stream (15) and steam (16).

In further embodiments wherein an additive is used in the finishing section, such as formaldehyde, any spent scrub liquid obtained from a scrubber of that finishing section is for example processed in a dedicated evaporation unit additional to the first and second vacuum evaporation stage, and the concentrated spent scrub liquid is for instance supplied to the finishing section to be solidified with the urea melt received by that finishing section.

In preferred embodiments, the prilling does not involve the use of formaldehyde and the spent scrub liquid contains no formaldehyde. In some embodiments, the second urea melt (10), supplied at least in part to the melamine plant (11), contains no formaldehyde; optionally the second urea melt also contains no ammonium nitrate and no ammonium sulphate.

Prilling of urea involves the solidification of urea melt droplets during free fall from the top of the prilling tower. The top of the prilling tower is provided with a urea melt droplet forming unit, such as a sprayer or rotating basket. Cooling air is provided from the bottom of the prilling tower and exhaust air is removed from the top. Solid urea product is collected and withdrawn from the bottom of the prilling tower. Prilling provides the advantage that because in some embodiments no additives are used, prills can be used as precursor for making DEF by dissolving in water, provided that the urea melt supplied to the prilling tower is of high purity, in particular has low biuret content.

The granulator is for example a spouted bed or fluidized bed granulation unit. An example granulator is a fluidized bed granulation unit, in particular with film spray nozzles.

The finishing section may also comprise, for instance, flash crystallization, such as described in US 2017/0204054A1. The finishing section may also comprise, for instance, a pelletizer, for example a pelletizer comprising a rotating belt, such as described in US 2009/0084149.

The finishing section for instance requires urea melt feed with less than 1.0 wt. % water, as is generally the case for prilling and some types of granulators.

A combination of two or more finishing sections in parallel is also possible.

Preferably, the method involves solidifying a part or all of the first urea melt to form solid urea product which contains less than 0.95 wt. % biuret, or less than 0.80 wt. %, while the urea plant is operated in the reduced load mode. Thereby the solid urea product can be dissolved by adding (demineralized water) to obtain DEF solution meeting the specifications for biuret content of ISO 22241-1:2006. The solidification is preferably performed in the finishing section.

Preferably, the urea (urea melt) supply of the finishing section (12) originates for at least 90 wt. %, or at least 95 wt. % from the first evaporator (7). Preferably, in the method no second urea melt (10) is supplied to the finishing section (12).

In some embodiments, the plant comprises the melamine plant, and is hence a plant for the production of urea and melamine.

Preferences and details for the plant as described in connection with the method also apply for the inventive plant. In the second vacuum evaporation stage (101) the first evaporator (7) and a second evaporator (9) are arranged in parallel, and both have an inlet connected to an outlet for concentrated urea solution (6) of the first vacuum evaporation stage (5). The plant comprises a liquid flow line for first urea melt from the first evaporator to the finishing section (12) and a liquid flow line (15) for first urea melt from the first evaporator to a melamine plant (11), and a liquid flow line for the second urea melt (10) from the second evaporator (9) to the melamine plant (11). The finishing section is preferably a prilling tower. The finishing section (12) is preferably connected for receiving urea melt exclusively from the first evaporator. The plant preferably comprises no liquid flow line for urea melt from the second evaporator (9) to the finishing section. This contributes to low biuret content of the solid urea product. The liquid flow lines may also be referred to as urea melt transport lines.

The invention also provides method of switching a urea plant, in particular an inventive urea plant, from a first operating mode to a second operating mode of the plant. The urea production rate, in particular in the urea synthesis section, in the second operating mode is at least 10% lower than in the first operating mode, as percentage of the production rate in the first operating mode, and preferably at least 20% lower or even at least 30% lower, and for instance not more than 50% lower.

The second operating mode hence corresponds to a reduced load operating mode. The first operating mode may refer to operation at design capacity, but also to operation with a urea production rate below or even above design capacity of the plant, in particular of the urea synthesis section. The method involves decreasing the flow rate of concentrated urea solution (6b) to the second evaporator (9) and keeping the flow rate of concentrated urea solution (6a) to the first evaporator (7) constant, or increasing the flow rate of concentrated urea solution to the first evaporator, or decreasing the flow rate of concentrated urea solution to the first evaporator in such an amount that the decrease, relative to the flow rate of the first evaporator in the first mode, is smaller than the decrease of the flow rate of concentrated urea solution to the second evaporator relative to the flow rate of the second evaporator in the first mode. In other words, $$R_{1,f}/R_{1,i} > R_{2,f}/R_{2,i},$$

(R1,f/R1,i>R2,f/R2,i), wherein R is the flow rate of urea solution (metric ton/hour), subscript 1 is the first evaporator, subscript 2 is the second evaporator, subscript f is the second operating mode, and subscript i is the first operating mode. Preferably, $$R_{1,f}/R_{1,i} > 1.2 * (R_{2,f}/R_{2,i})$$

(R1, f/R1, i > 1.2 * (R2, f/R2, i)).

This provides the advantage that the increase of the residence time of the urea solution in the first evaporator, caused by the switch from the first to the second operating mode, if any, is smaller is than the increase of the residence time of the urea solution in the second evaporator. Accordingly, the increase in biuret formation in the second vacuum evaporation stage in the second operating mode is localized in the second evaporator and does not negatively affect the quality of the solid urea product.

Preferably, in the second mode, a part or all of the second urea melt (10) from the second evaporator (9) is supplied to the melamine plant (11), and a part or all of the first urea melt (8) from the first evaporator (7) is supplied to the finishing section (12). Preferably, in the second mode, a first part of the first urea melt (8) is supplied to the finishing section (12) and a second part of the first urea melt (8) is supplied to the melamine plant (11). Optionally, both the first and second evaporator are used in the second operating mode. Optionally, only the first evaporator is used in the second operating mode, i.e. in some embodiments $R_{2,f}$ is nil.

Preferably, the urea melt flow rate from the first and second evaporator to the melamine plant (11) in the second mode is at least 80% or at least 90% of said flow rate in the first mode, most preferably kept the same. Preferably, the decrease in urea production rate, as percentage of urea production rate in the first operating mode, is larger than the decrease, if any, of the urea melt flow rate from the first and second evaporator to the melamine plant (11), and larger than decrease, if any, in the urea melt flow rate from the second evaporator (9) to the finishing section, all decreases from the first to second operating mode and as percentage of the flow rate in the first mode. This enable stable operation of the melamine plant. The inventive urea plant is preferably capable of switching from the first to the second operating mode and vice versa.

Advantageously, no mechanical modifications have to be made in the second vacuum evaporation stage during the switching from the first to second mode, which contributes to advantageous simple switching.

This method of switching a urea plant, in particular an inventive urea plant, from a first operating mode to a second operating mode of the plant, is preferably carried out in a plant for the production of urea, comprising: a urea production section (100) comprising a synthesis section (1) and a recovery section (2), a first vacuum evaporation stage (5) receiving urea solution from the urea production section, a second vacuum evaporation stage (101) receiving concentrated urea solution from the first vacuum evaporation stage, comprising a first evaporator (7) and a second evaporator (9) arranged in parallel, both receiving concentrated urea solution from the first vacuum evaporation stage, wherein the first evaporator has an outlet (8) for a first urea melt connected to a finishing section (12) and to a melamine plant (11), and wherein the second evaporator (9) has an outlet (10) for a second urea melt connected to said melamine plant (11). More preferably, the plant comprises the melamine plant, and is also suitable for the production of melamine, and further comprises the liquid flow line for the second urea melt from the second evaporator (9) to said melamine plant (11).

The term 'carbamate', as used herein, refers to ammonium carbamate, as that term is used in the field of urea production. In aqueous carbamate streams, the component can be present as carbonate species. Amounts of $NH_3$ and $CO_2$ for aqueous streams include the amounts present as carbonate species.

As used herein, for process streams of the urea plant (i.e. not for steam lines and not for melamine plants), high pressure (HP) is above 100 bar, for instance 120 to 300 bar, for example 140 to 200 bar. Medium pressure (MP) is for example 10 to 80 bar (including intermediate pressure of 30 to 70 bar), in particular 15 to 30 bar, and low pressure (LP)

is for example 0 to 10 bar, in particular 1 to 8 bar or 2 to 5 bar. All pressures are bar absolute (bara).

The terms 'typical', 'suitable' and 'in particular' and derived forms are used to indicate features that can be used in some embodiments but that are not mandatory. Also preferred features are not mandatory.

The term 'melamine off-gas' as used herein indicates off-gas from the melamine production section and refers to a gas stream mainly containing $NH_3$, $CO_2$, and possibly $H_2O$.

The term 'first' as used herein for a unit or step permits the presence of further, upstream, instances of such unit or step.

Aspects of the invention will now be illustrated with the following example, which does not limit the invention or the claims.

EXAMPLE 1

A urea plant coupled to a melamine plant as illustrated in FIG. 1 was operated as indicated in Table 1, with three configurations A, B, and C in the second mode. The urea production rate is higher in the first mode than in the second mode. The plant can switch from the first mode to the second mode and vice versa. T indicates metric ton.

TABLE 1

| Flow line or unit | | | Second mode | | |
|---|---|---|---|---|---|
| (FIG. 1) | | First mode | A | B | C |
| 1 | Production rate (%) | 100 | 84 | 70 | 60 |
| 2 | t urea/hour | 100 | 84 | 70 | 60 |
| 6 | biuret wt. %* | 0.55 | 0.61 | 0.66 | 0.71 |
| 6a | t urea/hour | 60 | 60 | 60 | 60 |
| 6b | t urea/hour | 40 | 24 | 10 | 0 |
| 7 | residence time (sec) | Y | Y | Y | Y |
| 9 | residence time (sec) | Z | 40/24*Z | 40/10*Z | — |
| 8 | biuret wt. %* | 0.55 + 0.16 | 0.61 + 0.16 | 0.66 + 0.16 | 0.71 + 0.16 |
| 10 | biuret wt. %* | 0.55 + 0.16 | 0.61 + 0.27 | 0.66 + 0.5 | — |
| 8 | t urea/hour | 60 | 60 | 60 | 60 |
| 16 | t urea/hour | about 60 | 50 | 50 | 60 |
| 11 | t urea feed/hour | 40 | 34 | 20 | 0 |

*as wt. % of urea; for 8 and 10 directly at outlet of evaporator.

The invention claimed is:

1. A method of operating a urea plant in a reduced load mode, the method comprising:
    operating a high pressure urea synthesis section of a urea plant in a reduced load mode;
    subjecting a urea solution stream from the urea synthesis section to purification in a recovery section to give purified urea solution;
    subjecting the purified urea solution to evaporation of water in a first vacuum evaporation stage, to give a first concentrated urea solution;
    subjecting a first part of the first concentrated urea solution to evaporation of water in a first evaporator of a second vacuum evaporation stage to form a first urea melt;
    subjecting a second part of the first concentrated urea solution to evaporation of water in a second evaporator of the second vacuum evaporation stage to form second urea melt;
    wherein the first evaporator is operated at a first operating capacity ratio, as percentage of a design capacity of the first evaporator, and wherein the second evaporator is operated at a second operating capacity ratio, as percentage of a design capacity of the second evaporator, wherein the second operating capacity ratio is lower than the first operating capacity ratio, and wherein the second evaporator has an outlet for the second urea melt connected with an inlet of a melamine plant.

2. The method according to claim 1, wherein the first evaporator is operated at 90-100% of the design capacity of the first operator, and the second evaporator is operated at 20-80% of the design capacity of the second evaporator.

3. The method according to claim 1, wherein the first evaporator is connected to a urea finishing section to form a solid urea product.

4. The method according to claim 3, wherein the urea finishing section is a prilling tower.

5. The method according to claim 3, wherein the urea supply of the finishing section originates for at least 90 wt. % from the first evaporator.

6. The method according to claim 1, comprising supplying a part of the first urea melt to the melamine plant.

7. The method according to claim 1, comprising supplying a part or all of the second urea melt to the melamine plant.

8. A plant for the production of urea, comprising:
    a urea production section comprising a synthesis section and a recovery section,
    a first vacuum evaporation stage receiving urea solution from the urea production section,
    a second vacuum evaporation stage receiving concentrated urea solution from the first vacuum evaporation stage, comprising a first evaporator and a second evaporator arranged in parallel, both receiving concentrated urea solution from the first vacuum evaporation stage, wherein the first evaporator has an outlet for a first urea melt connected to a finishing section and to a melamine plant, and wherein the second evaporator has an outlet for a second urea melt connected to said melamine plant.

9. The plant according to claim 8 wherein the finishing section is a prilling tower.

10. The plant according to claim 9, wherein the finishing section is connected for receiving urea melt exclusively from the first evaporator.

11. A plant according to claim 8 suitable for the production of urea and melamine, comprising said melamine plant and a liquid flow line for the second urea melt from said outlet of the second evaporator to the melamine plant.

12. A method of switching a urea plant according to claim 8 from a first mode to a second mode wherein the urea production rate is higher in the first mode than in the second mode, the method comprising:

decreasing a flow rate of concentrated urea solution to the second evaporator;

and keeping a flow rate of concentrated urea solution to the first evaporator constant, or increasing a flow rate of concentrated urea solution to the first evaporator, or decreasing a flow rate of concentrated urea solution to the first evaporator in such an amount that the decrease, relative to the flow rate of the first evaporator in the first mode, is smaller than the decrease of the flow rate of concentrated urea solution to the second evaporator relative to the flow rate of the second evaporator in the first mode.

13. The method according to claim 12, wherein in the second mode, a part or all of the second urea melt from the second evaporator is supplied to the melamine plant in the second mode, and a part or all of the first urea melt from the first evaporator is supplied to the finishing section.

14. The method according to claim 13, wherein in the second mode, a first part of the first urea melt is supplied to the finishing section and a second part of the first urea melt is supplied to the melamine plant.

15. The method according to claim 14, wherein the urea melt flow rate to the melamine plant in the second mode is at least 80% of the urea melt flow rate to the melamine plant in the first mode.

* * * * *